United States Patent [19]
Nye

[11] Patent Number: 5,969,172
[45] Date of Patent: Oct. 19, 1999

[54] SILICONE SOLVENTS FOR ANTIPERSPIRANT SALTS

[75] Inventor: Susan A. Nye, Feura Bush, N.Y.

[73] Assignee: General Electric Company, Pittsfield, Mass.

[21] Appl. No.: 09/096,792

[22] Filed: Jun. 12, 1998

[51] Int. Cl.[6] .................................................. C07F 7/08
[52] U.S. Cl. ............................ 556/445; 424/66; 424/68; 424/401
[58] Field of Search ....................... 556/445; 4201/401, 4201/66, 68

[56] References Cited

U.S. PATENT DOCUMENTS

| | | |
|---|---|---|
| 3,405,153 | 10/1968 | Jones et al. . |
| 3,420,932 | 1/1969 | Jones et al. . |
| 3,523,130 | 8/1970 | Jones et al. . |
| 3,538,137 | 11/1970 | Viventi ..................................... 556/445 |
| 3,715,334 | 2/1973 | Karstedt . |
| 3,775,452 | 11/1973 | Karstedt . |
| 3,814,730 | 6/1974 | Karstedt . |
| 3,947,556 | 3/1976 | Jones et al. . |
| 4,359,456 | 11/1982 | Gosling et al. . |
| 4,431,789 | 2/1984 | Okazaki et al. ..................... 556/445 X |
| 4,775,528 | 10/1988 | Callaghan et al. . |
| 4,781,917 | 11/1988 | Luebbe et al. . |
| 4,839,443 | 6/1989 | Akutsu et al. ....................... 556/445 X |
| 4,859,446 | 8/1989 | Abrutyn et al. . |
| 4,871,525 | 10/1989 | Giovanniello et al. . |
| 4,900,534 | 2/1990 | Inward . |
| 4,944,933 | 7/1990 | Inward . |
| 5,144,054 | 9/1992 | Shioya et al. ............................ 556/445 |
| 5,202,115 | 4/1993 | Vincenti et al. . |
| 5,234,677 | 8/1993 | Murray et al. . |
| 5,296,623 | 3/1994 | Katsoulis et al. . |
| 5,306,838 | 4/1994 | Shioya et al. ............................ 556/445 |
| 5,330,751 | 7/1994 | Curtin et al. . |
| 5,463,098 | 10/1995 | Giovanniello et al. . |
| 5,643,558 | 7/1997 | Provancal et al. . |
| 5,698,654 | 12/1997 | Nye et al. . |

*Primary Examiner*—Paul F. Shaver
*Attorney, Agent, or Firm*—Kenneth S. Wheelock; Michelle Bugbee

[57] ABSTRACT

Silicone compositions that are functionalized with 1,2 or 1,3 glycol bearing substituents render antiperspirant salts soluble, partially soluble therein or partially miscible therewith. Such functionalized silicones in conjunction with antiperspirant salts produce clear antiperspirant gel sticks.

27 Claims, No Drawings

SILICONE SOLVENTS FOR ANTIPERSPIRANT SALTS

FIELD OF THE INVENTION

The present invention relates to new silicone compositions that are functionalized wherein antiperspirant salts are rendered partially soluble therein or are rendered partially miscible therewith.

BACKGROUND OF THE INVENTION

Enhanced efficacy aluminum and aluminum-zirconium antiperspirant salts are well known and are described, for example, U.S. Pat. No. 4,359,456; U.S. Pat. No. 4,775,528; U.S. Pat. No. 4,859,446, U.S. Pat. No. 4,871,525; U.S. Pat. No. 4,900,534; U.S. Pat. No. 4,944,933; U.S. Pat. No. 5,202,115; U.S. Pat. No. 5,234,677; U.S. Pat. No. 5,296,623; and U.S. Pat. No. 5,330,751. These enhanced salts are also known to rapidly revert back to their non-enhanced state in solution, particularly at concentrations greater than 20%. Consequently, the enhanced antiperspirant salts are generally only available in powder form.

A number of references describe various ways of making alcohol soluble antiperspirant actives. These references include, for example, U.S. Pat. No. 3,405,153; U.S. Pat. No. 3,420,932; U.S. Pat. No. 3,523,130; and U.S. Pat. No. 3,947,556. In each case concentrated solutions of the antiperspirant active (i.e., in the 40 to 50% range) are employed as a starting material and the product is obtained as a powder, which must then be redissolved in the desired alcohol solution. Such techniques pre-date the availability of enhanced efficacy salts and are not believed to be applicable thereto as they would likely cause reversion to the non-enhanced state. An alcohol soluble complex of aluminum chlorohydrate and propylene glycol may be prepared by spray drying a propylene glycol solution of the aluminum chlorohydrate.

Two methods of making polyhydric alcohol solutions of antiperspirant salts have been described. In one method a powdered antiperspirant salt, which may be an enhanced efficacy salt, is dissolved directly in a polyhydric alcohol, such as propylene glycol. In the other case, the polyhydric alcohol contains about 10 to 20% water and the antiperspirant salt has a water content greater than 10%.

A method of making polyhydric alcohol solutions of antiperspirant salts which are free of unbound water is described in U.S. Pat. No. 4,781,917. In that method, a powdered antiperspirant salt, which may be an enhanced efficacy salt, is dissolved in water (a 50% solution is exemplified), a polyhydric alcohol, such as propylene glycol, is added to the aqueous solution, then all of the water is removed by heating under vacuum. A method of making a propylene glycol solution of an aluminum-zirconium antiperspirant salt neutralized with zinc glycinate has also been described. An aqueous solution of aluminum chlorohydrate is refluxed in the presence of a small amount of propylene glycol, the solution is cooled to 70° C., zirconyl hydroxychloride-gly is added, the solution is cooled to 40° C., then zinc glycinate followed by propylene glycol is added. This solution is then distilled under vacuum to remove water, leaving a 30% by weight solution of antiperspirant active in propylene glycol.

The above-described methods suffer from a number of deficiencies. First, many of them are not efficient because they utilize a powdered material. Isolation of a powdered antiperspirant salt from solution is time consuming and costly. Second, it is believed that these methods will likely result in some loss of efficacy and/or will not provide clear solutions. Antiperspirant salts which have been obtained by spray drying are notoriously difficult to redissolve as clear solutions. Moreover, any method which requires an aqueous salt concentration over 20% will likely suffer some loss in efficacy.

SUMMARY OF THE INVENTION

I now disclose that by means of a new silicone composition, antiperspirant salts may be dissolved or dispersed in the silicone of the present invention and cosmetic, deodorant, antiperspirant, or personal care compositions may be formulated therewith. This new silicone composition enables the formulation of antiperspirant salt containing cosmetic, deodorant, antiperspirant, or personal care compositions that are transparent.

Thus the present invention provides for a silicone compound having the formula:

$$M_a M'_b D_c D'_d T_e T'_f Q_g$$

where the subscripts a, c, d, e, f and g are zero or a positive integer, subject to the limitation that the sum of the subscripts b, d and f is one or greater; where M has the formula:

$$R^1{}_3 SiO_{1/2},$$

where each $R^1$ is independently a monovalent hydrocarbon radical having from one to forty carbon atoms; M' has the formula:

$$R^2{}_{3-h} R^3{}_h SiO_{1/2},$$

where each $R^2$ is independently a monovalent hydrocarbon radical having from one to forty carbon atoms, $R^3$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript h is 1, 2 or 3; D has the formula:

$$R^4{}_2 SiO_{2/2},$$

where each $R^4$ is independently a monovalent hydrocarbon radical having from one to forty carbon atoms; D' has the formula:

$$R^5{}_{2-i} R^6{}_i SiO_{2/2}$$

where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2; T has the formula:

$$R^7 SiO_{3/2},$$

where each $R^7$ is a monovalent hydrocarbon radical having from one to forty carbon atoms; T' has the formula:

$$R^8 SiO_{3/2},$$

where $R^8$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and Q has the formula $SiO_{4/2}$.

DETAILED DESCRIPTION OF THE INVENTION

The present invention comprises a silicone composition having the formula:

$$M_aM'_bD_cD'_dT_eT'_fQ_g$$

where the subscripts a, c, d, e, f and g are zero or a positive integer, subject to the limitation that the sum of the subscripts b, d and f is one or greater or alternatively the subscript b is a positive integer of 2 or greater and the subscript c is a positive integer of 1 or greater; where M has the formula:

$$R^1{}_3SiO_{1/2},$$

where each $R^1$ is independently a monovalent hydrocarbon radical having from one to forty carbon atoms; M' has the formula:

$$R^2{}_{3-h}R^3{}_hSiO_{1/2},$$

where each $R^2$ is independently a monovalent hydrocarbon radical having from one to forty carbon atoms, $R^3$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript h is 1, 2 or 3; D has the formula:

$$R^4{}_2SiO_{2/2},$$

where each $R^4$ is independently a monovalent hydrocarbon radical having from one to forty carbon atoms; D' has the formula:

$$R^5{}_{2-i}R^6{}_iSiO_{2/2}$$

where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2; T has the formula:

$$R^7SiO_{3/2},$$

where each $R^7$ is a monovalent hydrocarbon radical having from one to forty carbon atoms; T' has the formula:

$$R^8SiO_{3/2},$$

where $R^8$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and Q has the formula $SiO_{4/2}$. The present invention also comprises the silicone composition of the present invention and a salt of aluminum or zirconium. More particularly the present invention is a cosmetic, deodorant, antiperspirant, or personal care composition that comprises the silicone composition of the present invention and a salt of aluminum or zirconium.

The compositions of the present invention are prepared by the hydrosilylation of an organohydrogen silicone having the formula:

$$M_aM^H{}_bD_cD^H{}_dT_eT^H{}_fQ_g$$

where the subscripts a, c, d, e, f and g are zero or a positive integer, subject to the limitation that the sum of the subscripts b, d and f is one or greater or alternatively the subscript b is a positive integer of 2 or greater and the subscript c is a positive integer of 1 or greater; where M has the formula:

$$R^1{}_3SiO_{1/2},$$

where each R' is independently a monovalent hydrocarbon radical having from one to forty carbon atoms; $M^H$ has the formula:

$$R^2{}_{3-h}H_hSiO_{1/2},$$

where each $R^2$ is independently a monovalent hydrocarbon radical having from one to forty carbon atoms; D has the formula:

$$R^4{}_2SiO_{2/2},$$

where each $R^4$ is independently a monovalent hydrocarbon radical having from one to forty carbon atoms; $D^H$ has the formula:

$$H_{2-i}R^6{}_iSiO_{2/2}$$

where each $R^6$ is independently a monovalent hydrocarbon radical having from one to forty carbon atoms; T has the formula:

$$R^7SiO_{3/2},$$

where each $R^7$ is a monovalent hydrocarbon radical having from one to forty carbon atoms; $T^H$ has the formula:

$$HSiO_{3/2};$$

and Q has the formula $SiO_{4/2}$ in the presence of $H_2(OH)CCH(OH)CH_2OCH_2CH=CH_2$ or $(HOCH_2)_2C(CH_2CH_3)CH_2OCH_2CH=CH_2$.

Hydrosilylation is accomplished in the presence of a suitable hydrosilylation catalyst. The catalyst preferred for use with these compositions are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979). Persons skilled in the art can easily determine an effective amount of platinum catalyst. Generally, an effective amount ranges from about 0.1 to 50 parts per million of the total organopolysiloxane composition.

The organohydrogen silicone compounds that are the precursors to the compounds of the present invention may be prepared by the process disclosed in U.S. Pat. No. 5,698,654 herewith specifically incorporated by reference. The '654 patent discloses a sequential catalysis of the ring opening polymerization of cyclic organosiloxanes using a base catalyst that can be neutralized by a subsequent redistribution and condensation catalyst such as a Lewis acid catalyst, preferably a phosphonitrilic compound, that permits the rapid synthesis of functionalized and poly-functionalized silicone copolymers.

It is to be noted that as pure compounds the subscripts describing the organohydrogen siloxane precursor and the hydrosilylation adduct of the present invention are integers as required by the various rules of chemical stoichiometry. As mixtures of compounds that are described by these formulas the subscripts will assume non-integral values, for the mixtures. The restrictions on the subscripts heretofore described for the stoichiometric subscripts of these compounds are for the pure compounds, not the mixtures. In a specific embodiment of the present invention, a preferred compound is $M'_b D_c$ where the subscript b is 2 and the subscript c ranges from 1 to 30, preferably from 2 to 20, more preferably from 3 to 10 and most preferably from 3 to 5.

Antiperspirant salts which may be used in the deodorant compositions of the present invention include any of the conventional aluminum, zirconium and aluminum-zirconium salts known to be useful in antiperspirant or deodorant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate). Preferred aluminum salts are those having the general formula:

$$Al_2(OH)_{6-z}X_z$$

wherein the anion X is Cl, Br, I or NO3, and z is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and z is about 1, such that the aluminum to chlorine mole ratio is about 1.9:1 to 2.1:1.

Preferred aluminum-zirconium salts are mixtures or complexes of the above-described aluminum salts with zirconium salts of the formula:

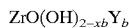

$$ZrO(OH)_{2-xb}Y_b$$

wherein the anion Y is Cl, Br, I, $NO_3$, or $SO_4$, x is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-x}Cl_x$ wherein x is about 1 to 2, preferably about 1.2 to about 1.9. The preferred aluminum-zirconium salts have an Al:Zr ratio of about 1.7 to about 12.5, most preferably about 2 to about 10, and a metal:(X+Y) ratio of about 0.73 to about 2.1, preferably about 0.9 to 1.5. A preferred salt is aluminum-zirconium chlorohydrate (i.e. X and Y are both Cl), which has an Al:Z ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine (Gly), typically with a glycine to zirconium (Gly:Zr) ratio of about 1:1 to 4:1. Aluminum zirconium salt complexes containing the neutral amino acid glycine are commonly designated glycinate salts and are typically abbreviated ZAG for zirconium (Z) aluminum (A) glycinate (G).

It is especially preferred to utilize enhanced efficacy aluminum and aluminum-zirconium antiperspirant salts in the gel sticks of the present invention. By "enhanced efficacy antiperspirant salts" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 higher. Any suitable HPLC technique may be employed provided that it is capable of resolving the Al component into five peaks. The enhanced efficacy (or activated) antiperspirant salts are well-known in the industry and are commercially available from several suppliers.

The antiperspirant salt is dissolved in the liquid vehicle or a portion of the liquid vehicle. The antiperspirant salt is dissolved or dispersed in a liquid vehicle or a portion of the liquid vehicle. The silicone compositions of the present invention provide a new liquid vehicle for the dissolution or dispersal of the antiperspirant or deodorant salts. Especially preferred are solubilized salts which have been partially neutralized by addition of a pH-raising agent to a pH of about 4.1 to 5.0, preferably about 4.3 to 4.8. Particularly preferred neutralized antiperspirant salts are those which contain an additional alkaline glycinate, such as sodium, potassium, or zinc glycinate. Such solubilized antiperspirant salts are described in U.S. Pat. No. 5,643,558 entitled Method Of Making Polyhydric Alcohol Solutions Of Enhanced Efficacy Antiperspirant Actives and in U.S. Pat. No. 5,463,098, the disclosures of which are incorporated herein by reference. An example of such a solubilized salt, which is partially neutralized with zinc glycinate, is Westchlor A2Z 8106 (Westwood Chemical Corp.). The preparation of a preferred solubilized antiperspirant salt is described in Example 1 below. The additional alkaline glycinate which is preferably included in the solubilized antiperspirant salt raises the pH of the antiperspirant salt and, as a result, reduces the degradation of the dibenzylidene alditol in the gel stick. It is generally preferred to add sufficient alkaline glycinate to the solubilized antiperspirant salt so as to raise the pH of an approximately 10% aqueous solution of the antiperspirant salt to about 4.1 to 5.0, preferably about 4.3 to 4.8. (The 10% aqueous solution may be an approximately 50:50 polyhydric alcohol:water solution.) Preferred deodorant or antiperspirant compositions which include such a partially neutralized salt will have a pH greater than 4.4, preferably about 4.7 to about 5.5, and more preferably about 4.8 to about 5.3. The pH of the finished composition can be measured by dissolving one part stick in ninety-nine parts water. The pH of the solubilized antiperspirant salt or of the resulting composition can, of course, be adjusted to the aforementioned preferred pH ranges with any pH-raising agent, or combination of pH-raising agents, provided that the agent or agents selected are soluble in the vehicle and do not adversely affect the optical properties or odor characteristics of the stick to a significant extent. Sufficient antiperspirant salt should be dissolved in the liquid vehicle so that the final composition, after all components are added, includes between about 1% and about 22%, preferably between about 2% and about 15%, of the antiperspirant salt by weight. It should be noted that reference throughout this application to weight percent of antiperspirant salt is intended to be calculated in accordance with the standard industry method, which includes bound water and glycine.

All U.S. patents referenced herein are herewith and hereby specifically incorporated by reference.

Experimental

Functionalized silicones were made by the hydrosilylation of an allyl modified 1,2-diol (mono-allyl glycerine) and 1,3-diol (trimethylolpropane mono allyl ether). The products were functionalized either on the backbone or on the termini. The table shows a comparison of these products contrasting their viscosities, miscibilities with the AP salt solution and relative feel of the product.

|  |  |  |  |  | Solubility | | |
| --- | --- | --- | --- | --- | --- | --- | --- |
| Product # | Structure | Function.[1] | % Silicone | Visc(cSt) | DPG[2] | ZAG/PG[3] | Feel |
| 1 | $MD_4'M$ | 1,3-DIOL | 37% |  | yes | yes | tacky |
| 2 | $M'D_3M'$ | 1,3-DIOL | 51% | 469 | yes | yes | silky |
| 3 | $MD_{6.4}D'_5M$ | 1,3-DIOL | 52% | 5100 | yes | yes | v.tacky |
| 4 | $MD_{10}D'_7M$ | 1,3-DIOL | 52% | 3700 | yes | yes | v.tacky |
| 5 | $M'D_3M'$ | 1,2-DIOL | 57% | 515 | yes | yes | v.silky |
| 6 | $M'D_5M'$ | 1,3-DIOL | 59% | 907 |  | no | silky |
| 7 | $MD_{6.4}D'_5M$ | 1,2-DIOL | 59% | 5480 | yes | yes | v.tacky |
| 8 | $MD_3D'_3M$ | 1,2-DIOL | 59% |  | yes | yes | tacky |
| 9 | $MD_7D'_3M$ | 1,3-DIOL | 61% | 1050 | no | no | tacky |
| 10 | $M'D_5M'$ | 1,2-DIOL | 66% | 630 | yes | yes | v.silky |
| 11 | $M'D_{7.5}M'$ | 1,3-DIOL | 66% | 746 |  | no | silky |
| 12 | $MD_7D'_3M$ | 1,2-DIOL | 69% |  | yes | no | tacky[4] |
| 13 | $M'D_{7.5}M'$ | 1,2-DIOL | 72% | 502 | yes | no | v.silky |
| 14 | $M'D_{10}M'$ | 1,3-DIOL | 72% | 240 | no | no | silky[4] |
| 15 | $M'D_{10}M'$ | 1,2-DIOL | 77% | 460 | yes | no | v.silky |
| 16 | $MD_{20}D'_3M$ | 1,3-DIOL | 78% |  | no | no | tacky[4] |
| 17 | $M'D_{25}M'$ | 1,2-DIOL | 88% | 422 | no | no | v.silky |

[1] 1,3-DIOL is TMPMAE and 1,2-DIOL is Mono-allyl glycerine.
[2] DPG = dipropylene glycol.
[3] ZAG = 28% Zirconium-aluminum glycine salt in propylene glycol.
[4] Product soluble in $D_5$.

Analyses

Viscosities were measured in Ostwald tube using appropriately-sized tubes to give flow times of 200–1000 seconds. For the high viscosity fluids (>2000 cPs) the measurements were made on a Brookfield Model DV-III Programmable Rheometer. The hydrosilylation reactions were followed by monitoring the disappearance of the silicon hydride absorbance at 2160 cm$^{-1}$ on a Nicolet 5DXB FTIR Spectrometer. Hydride analyses of the starting silicone hydride fluids were performed gasiometrically with sodium t-butoxide in t-butanol as the titrant. Percent solids were measured by heating 1 gram of sample in an aluminum pan in an oven at 150° C. for 45 minutes.

Syntheses

Mono allyl glycerine (MAG) was obtained from FLUKA Chemical Company, Trimethylol propane mono-allyl ether (TMPMAE) was obtained from Perstorp Chemical Company and the antiperspirant salt solution from Westwood Chemical Company.

1,3-DIOL–functionalized Silicone Syntheses(Product #3)

A 3 liter flask was charged with TMPMAE (918.4 g, 5.34 mol) and cyclohexane (526.0 g). The flask was equipped with a dean stark trap, a condenser, a thermometer, a stir bar and a nitrogen sparge. The mixture was heated to reflux temperature which was about 90° C., to azeotropically dry the reaction. The reactor was cooled to 80° C. and 0.23 g of Karstedt's catalyst was added to the mixture. An addition funnel was charged with the hydride ($MD_{6.4}D^H{}_5M$, 492.6 g, 2.63 mol SiH) which was slowly added over a 2 hour period to control the exotherm. The reaction was stirred at 90° C. for an additional 2–3 hours while following hydride loss by FTIR. The reaction was stripped for 3 hours with full vacuum at 130° C. until reaching 90% solids. The final viscosity was 5100 cPs and the refractive index (RI) was 1.4549.

1,2-DIOL—functionalized Silicone Synthesis: (Product #13)

A 500 ml flask was charged with MAG (76.66 g, 0.58 moles), cyclohexane (74.54 g), and Karstedt's catalyst (34.3 mg) was added. The mixture was heated to 85° C. An addition funnel was charged with the hydride fluid ($M^H D_{7.5} M^H$, 100.03 g, 0.29 mol SiH). The hydride fluid was added over a 45 minute period and the temperature was maintained at 85° C. for two additional hours. The reaction was tested by FTIR for completion. Solvent was stripped out with a vacuum pump at 130° C. with a nitrogen sparge for five hours. The product had a final solids of 99%, viscosity was 502 cSt and RI was 1.430.

Clear AP Stick Formulation #1

To a 2 oz jar was added Product #7 (20.04 g) and dibenzylidene sorbitol, DBS, (0.83 g) was added gingerly. The mixture was heated to 190° C. before the DBS dissolved. The heated mixture was cooled to 135° C. and added to a heated (50° C.) solution of 28% ZAG salt in propylene glycol (20 g). A solid stick was produced which felt tacky on the forearm.

Clear AP Stick Formulation #2

To a 2 oz jar was added Product #5 (98 g) and dibenzylidene sorbitol, DBS, (2.00 g) was added gingerly. The mixture was heated to 170° C. before the DBS dissolved. The heated mixture was cooled to 135° C. and added to a heated (50° C.) solution of 28% ZAG salt propylene glycol (100 g). A solid stick was produced which felt smooth and dry by comparison when tested on the forearm.

Having described the invention that which is claimed is:

1. A silicone compound having the formula:

$$M_a M'_b D_c D'_d T_e T'_f Q_g$$

where the subscripts a, c, d, e, f and g are zero or a positive integer, subject to the limitation that the sum of the subscripts b, d and f is one or greater; where M has the formula:

$$R^1{}_3 SiO_{1/2},$$

where each $R^1$ is independently a monovalent hydrocarbon radical having from one to forty carbon atoms; M' has the formula:

$$R^2{}_{3-h} R^3{}_h SiO_{1/2},$$

where each $R^2$ is independently a monovalent hydrocarbon radical having from one to forty carbon atoms, $R^3$ is $(HOCH_2)_2 C(CH_2 CH_3) CH_2 OCH_2 CH_2 CH_2$— and the subscript h is 1, 2 or 3; D has the formula:

$$R^4{}_2 SiO_{2/2},$$

where each $R^4$ is independently a monovalent hydrocarbon radical having from one to forty carbon atoms; D' has the formula:

$R^5{}_{2-i}R^6{}_iSiO_{2/2}$ where each $R^6$ is independently a monovalent hydrocarbon radical having from one to forty carbon atoms, $R^5$ is $(HOCH_2)_2C(CH_2CH_3)CH_2OCH_2CH_2CH_2—$ and the subscript i is 1 or 2; T has the formula:

$R^7SiO_{3/2}$, where each $R^7$ is a monovalent hydrocarbon radical having from one to forty carbon atoms; T' has the formula:

$R^8SiO_{3/2}$, where $R^8$ is $(HOCH_2)_2C(CH_2CH_3)CH_2OCH_2CH_2CH_2—$ and Q has the formula $SiO_{4/2}$.

2. The compound of claim 1 wherein g is zero.
3. The compound of claim 2 wherein f is zero.
4. The compound of claim 3 wherein e is zero.
5. The compound of claim 4 wherein d is zero.
6. The compound of claim 4 wherein c is zero.
7. The compound of claim 4 wherein b is zero.
8. The compound of claim 4 wherein a is zero.
9. The compound of claim 5 wherein c ranges from 3 to 25.
10. The compound of claim 6 wherein d ranges from 3 to 25.
11. A mixture of silicone compounds comprising a silicone compound having the formula:

$M_aM'_bD_cD'_dT_eT'_fQ_g$ where the subscripts a, c, d, e, f and g are zero or a positive integer, subject to the limitation that the sum of the subscripts b, d and f is one or greater; where M has the formula:

$R^1{}_3SiO_{1/2}$, where each $R^1$ is independently a monovalent hydrocarbon radical having from one to forty carbon atoms; M' has the formula:

$R^2{}_{3-h}R^3{}_hSiO_{1/2}$, where each $R^2$ is independently a monovalent hydrocarbon radical having from one to forty carbon atoms, $R^3$ is $(HOCH_2)_2C(CH_2CH_3)CH_2OCH_2CH_2CH_2—$ and the subscript h is 1, 2 or 3; D has the formula:

$R^4{}_2SiO_{2/2}$, where each $R^4$ is independently a monovalent hydrocarbon radical having from one to forty carbon atoms; D' has the formula:

$R^5{}_{2-i}R^6{}_iSiO_{2/2}$ where each $R^6$ is independently a monovalent hydrocarbon radical having from one to forty carbon atoms, $R^5$ is $(HOCH_2)_2C(CH_2CH_3)CH_2OCH_2CH_2CH_2—$ and the subscript i is 1 or 2; T has the formula:

$R^7SiO_{3/2}$, where each $R^7$ is a monovalent hydrocarbon radical having from one to forty carbon atoms; T' has the formula:

$R^8SiO_{3/2}$, where $R^8$ is $(HOCH_2)_2C(CH_2CH_3)CH_2OCH_2CH_2CH_2—$ and Q has the formula $SiO_{4/2}$.

12. The compound of claim 11 wherein g is zero.
13. The compound of claim 12 wherein f is zero.
14. The compound of claim 13 wherein e is zero.
15. The compound of claim 14 wherein d is zero.
16. The compound of claim 14 wherein c is zero.
17. The compound of claim 14 wherein b is zero.
18. The compound of claim 14 wherein a is zero.
19. The compound of claim 15 wherein c ranges from 3 to 25.
20. The compound of claim 16 wherein d ranges from 3 to 25.
21. A silicone compound having the formula:

$M_aM'_bD_cD'_dT_eT'_fQ_g$ where the subscripts a, c, d, e, f and g are zero or a positive integer, the subscript b is a positive integer of 2 or greater and the subscript c is a positive integer of 1 or greater; where M has the formula:

$R^1{}_3SiO_{1/2}$, where each $R^1$ is independently a monovalent hydrocarbon radical having from one to forty carbon atoms; M' has the formula:

$R^2{}_{3-h}R^3{}_hSiO_{1/2}$, where each $R^2$ is independently a monovalent hydrocarbon radical having from one to forty carbon atoms, $R^3$ is a monovalent hydrocarbon radical selected from the group consisting of $H_2(OH)CCH(OH)CH_2OCH_2CH_2CH_2—$ and $(HOCH_2)_2C(CH_2CH_3)CH_2OCH_2CH_2CH_2—$ and the subscript h is 1, 2 or 3; D has the formula:

$R^4{}_2SiO_{2/2}$, where each $R^4$ is independently a monovalent hydrocarbon radical having from one to forty carbon atoms; D' has the formula:

$R^5{}_{2-i}R^6{}_iSiO_{2/2}$ where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2—$ and $(HOCH_2)_2C(CH_2CH_3)CH_2OCH_2CH_2CH_2—$ and the subscript i is 1 or 2; T has the formula:

$R^7SiO_{3/2}$, where each $R^7$ is a monovalent hydrocarbon radical having from one to forty carbon atoms; T' has the formula:

$R^8SiO_{3/2}$, where $R^8$ is a monovalent hydrocarbon radical selected from the group consisting of $H_2(OH)CCH(OH)CH_2OCH_2CH_2CH_2—$ and $(HOCH_2)_2C(CH_2CH_3)CH_2OCH_2CH_2CH_2—$ and Q has the formula $SiO_{4/2}$.

22. A personal care composition comprising the compound of claim 1 and further comprising a salt of aluminum or zirconium.
23. A personal care composition comprising the compound of claim 9 and further comprising a salt of aluminum or zirconium.
24. A personal care composition comprising the compound of claim 10 and further comprising a salt of aluminum or zirconium.

25. A personal care composition comprising: a silicone compound having the formula:

$$M_aM'_bD_cD'_dT_eT'_fQ_g$$

where the subscripts a, c, d, e, f and g are zero or a positive integer, subject to the limitation that the sum of the subscripts b, d and f is one or greater; where M has the formula:

$$R^1_3SiO_{1/2},$$

where each $R^1$ is independently a monovalent hydrocarbon radical having from one to forty carbon atoms; M' has the formula:

$$R^2_{3-h}R^3_hSiO_{1/2},$$

where each $R^2$ is independently a monovalent hydrocarbon radical having from one to forty carbon atoms, $R^3$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript h is 1, 2 or 3; D has the formula:

$$R^4_2SiO_{2/2},$$

where each $R^4$ is independently a monovalent hydrocarbon radical having from one to forty carbon atoms; D' has the formula:

$$R^5_{2-i}R^6_iSiO_{2/2}$$

where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2; T has the formula:

$$R^7SiO_{3/2},$$

where each $R^7$ is a monovalent hydrocarbon radical having from one to forty carbon atoms; T' has the formula:

$$R^8SiO_{3/2},$$

where $R^8$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and Q has the formula $SiO_{4/2}$; and a salt of aluminum or zirconium.

26. A personal care composition comprising: a silicone compound having the formula:

$$M_aM'_bD_cD'_dT_eT'_fQ_g$$

where the subscripts a, b and c are a positive integer, the subscripts d, e, f and g are zero, and the subscript c ranges from 3 to 25; where M has the formula:

$$R^1_3SiO_{1/2},$$

where each $R^1$ is independently a monovalent hydrocarbon radical having from one to forty carbon atoms; M' has the formula:

$$R^2_{3-h}R^3_hSiO_{1/2},$$

where each $R^2$ is independently a monovalent hydrocarbon radical having from one to forty carbon atoms, $R^3$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript h is 1, 2 or 3; D has the formula:

$$R^4_2SiO_{2/2},$$

where each $R^4$ is independently a monovalent hydrocarbon radical having from one to forty carbon atoms; D' has the formula:

$$R^5_{2-i}R^6_iSiO_{2/2}$$

where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2; T has the formula:

$$R^7SiO_{3/2},$$

where each $R^7$ is a monovalent hydrocarbon radical having from one to forty carbon atoms; T' has the formula:

$$R^8SiO_{3/2},$$

where $R^8$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and Q has the formula $SiO_{4/2}$; and a salt of aluminum or zirconium.

27. A personal care composition comprising: a silicone compound having the formula:

$$M_aM'_bD_cD'_dT_eT'_fQ_g$$

where the subscripts a, b and d are a positive integer, the subscripts c, e, f and g are zero, and the subscript c ranges from 3 to 25; where M has the formula:

$$R^1_3SiO_{1/2},$$

where each $R^1$ is independently a monovalent hydrocarbon radical having from one to forty carbon atoms; M' has the formula:

$$R^2_{3-h}R^3_hSiO_{1/2},$$

where each $R^2$ is independently a monovalent hydrocarbon radical having from one to forty carbon atoms, $R^3$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript h is 1, 2 or 3; D has the formula:

$$R^4_2SiO_{2/2},$$

where each $R^4$ is independently a monovalent hydrocarbon radical having from one to forty carbon atoms; D' has the formula:

$$R^5_{2-i}R^6_iSiO_{2/2}$$

where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2; T has the formula:

$$R^7SiO_{3/2},$$

where each $R^7$ is a monovalent hydrocarbon radical having from one to forty carbon atoms; T' has the formula:

$$R^8SiO_{3/2},$$

where $R^8$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and Q has the formula $SiO_{4/2}$; and a salt of aluminum or zirconium.

* * * * *

(12) REEXAMINATION CERTIFICATE (4602nd)
United States Patent
Nye

(10) Number: US 5,969,172 C1
(45) Certificate Issued: *Jun. 18, 2002

(54) SILICONE SOLVENTS FOR ANTIPERSPIRANT SALTS

(75) Inventor: Susan A. Nye, Feura Bush, NY (US)

(73) Assignee: General Electric Company, Schenectady, NY (US)

Reexamination Request:
No. 90/005,819, Sep. 11, 2000

Reexamination Certificate for:
Patent No.: 5,969,172
Issued: Oct. 19, 1999
Appl. No.: 09/096,792
Filed: Jun. 12, 1998

(*) Notice: This patent is subject to a terminal disclaimer.

(51) Int. Cl.⁷ ................................................ C07F 7/08
(52) U.S. Cl. ...................... 556/445; 424/66; 424/68; 424/401
(58) Field of Search ...................... 556/445; 424/66, 424/68, 401

(56) References Cited

U.S. PATENT DOCUMENTS

| | | | |
|---|---|---|---|
| 3,317,460 A | 5/1967 | Clark et al. ................ | 260/46.5 |
| 4,431,789 A | 2/1984 | Okazaki et al. ............... | 528/15 |
| 4,908,228 A | 3/1990 | Lo ............................. | 427/54.1 |
| 5,144,054 A | 9/1992 | Shioya et al. ............... | 556/445 |
| 5,160,732 A | 11/1992 | Katsoulis et al. ............. | 424/68 |
| 5,262,155 A | 11/1993 | Vincent et al. .......... | 424/78.02 |
| 5,306,838 A | 4/1994 | Shioya et al. ............... | 556/445 |
| 5,403,580 A | 4/1995 | Bujanowski et al. ......... | 424/65 |
| 5,969,172 A | 10/1999 | Nye ........................... | 556/445 |
| 6,268,519 B1 * | 7/2001 | Nye ........................... | 556/445 |

FOREIGN PATENT DOCUMENTS

| | | |
|---|---|---|
| EP | 0404532 A1 | 12/1990 |
| EP | 1 074 577 A1 | 2/2001 |

* cited by examiner

*Primary Examiner*—Porfirio Nazario-Gonzalez

(57) ABSTRACT

Silicone compositions that are functionalized with 1,2 or 1,3 glycol bearing substituents render antiperspirant salts soluble, partially soluble therein or partially miscible therewith. Such functionalized silicones in conjunction with antiperspirant salts produce clear antiperspirant gel sticks.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–9, 11–19 and 21 are cancelled.

Claims 10, 20, 22, 23 and 25–27 are determined to be patentable as amended.

Claim 24, dependent on an amended claim, is determined to be patentable.

10. [The compound of claim 6 wherein] *A silicone compound having the formula :*

$$M_a D'_d$$

wherein the subscripts a is zero or a positive integer and d [ranges] *is an integer in the range* from 3 to 25, inclusive;

M has the formula: $R^1_3 SiO_{1/2}$, wherein each $R^1$ is independently a monovalent hydrocarbon radical having from one to forty carbon atoms;

D' has the formula: $R^5_{2-i}R^6_i SiO_{2/2}$, wherein each $R^6$ is independently a monovalent hydrocarbon radical having from one to forty carbon atoms, $R^5$ is $(HOCH_2)_2C(CH_2CH_3)CH_2OCH_2CH_2CH_2$— and the subscript i is 1 or 2.

20. [The compound of claim 16 wherein] *A mixture of silicone compounds comprising a silicone compound having the formula:*

$$M_a D'_d$$

wherein the subscripts a is zero or a positive integer and d *is in the* range[s] from 3 to 25 *inclusive*;

M has the formula; $R^1_3 SiO_{1/2}$, where each $R^1$ is independently a monovalent hydrocarbon radical having from one to forty carbon atoms;

D' has the formula: $R^5_{3-i}R^6_i SiO_{2/2}$ where each $R^6$ is independently a monovalent hydrocarbon radical having from one to forty carbon atoms, $R^5$ is $(HOCH_2)_2C(CH_2CH_3)CH_2OCH_2CH_2CH_2$- and the subscript i is 1 or 2.

22. A personal care composition [comprising the compound of claim 1 and further] comprising a salt of aluminum or zirconium, *and a silicone compound, wherein said silicon compound has a viscosity greater than about 240 cSts at 25° C., and wherein said silicone compound has the formula:*

$$M_a M'_b D_c D'_d T_e T'_f Q_g,$$

wherein the subscripts a, c, d, e, f, and g are zero or a positive integer, subject to the limitation that the sum of the subscripts b, d, and f is one or greater;

where M has the formula: $R^1_3 SiO_{1/2}$, where each $R^1$ is independently a monovalent hydrocarbon radical having from one to forty carbon atoms;

M' has the formula: $R^2_{3-h}R^3_h SiO_{1/2}$, where each $R^2$ is independently a monovalent hydrocarbon radical having from one to forty carbon atoms, $R^3$ is $(HOCH_2)_2C(CH_2CH_3)CH_2OCH_3CH_2CH_2$_ and the subscript h is 1, 2, or 3;

D has the formula: $R^4_2 SiO_{2/2}$, where each $R^4$ is independently a monovalent hydrocarbon radical having from one to forty carbon atoms;

D' has the formula: $R^5_{2-i}R^6_i SiO_{2/2}$, where each $R^6$ is independently a monovalent hydrocarbon radical having from one to forty carbon atoms $R^5$ is $(HOCH_2)_2C(CH_2CH_3)CH_2OCH_2CH_2CH_2$— and the subscript i is 1 or 2;

T has the formula: $R^7 SiO_{3/2}$, where each $R^7$ is a monovalent hydrocarbon radical having from one to forty carbon atoms;

T' has the formula: $R^8 SiO_{3/2}$, where $R^8$ is $(HOCH_2)_3C(CH_2CH_3)CH_2OCH_2CH_2CH_2$— and Q has the formula: $SiO_{4/2}$.

23. [A] *The* personal care composition [comprising the compound of claim 9 and further comprising a salt of aluminum or zirconium] *of claim 22, wherein d=e=f=g=0, and c is in the range from 3 to 25, inclusive.*

25. A personal care composition comprising: a silicone compound having *a viscosity greater than about 240 cSts at 25° C., and wherein said silicone compound has* the formula:

$$M_a M'_b D_c D'_d T_e T'_f Q_g,$$

where the subscripts a, c, d, e, f, and g are zero or a positive integer, subject to the limitation that the sum of the subscripts b, d and f is one or greater;

where M has the formula: $R^1_3 SiO_{1/2}$, where each $R^1$ is independently a monovalent hydrocarbon radical having from one to forty carbon atoms;

M' has the formula: $R^2_{3-h}R^3_h SiO_{1/2}$, where each $R^2$ is independently a monovalent hydrocarbon radical having from one to forty carbon atoms, $R^3$ *is a monovalent hydrocarbon radical selected from the group consisting of* $H_2(OH)CCH(OH)CH_2OCH_2CH_2CH_2$— *and* $(HOCH_2)_2C(CH_2CH_3)CH_2OCH_2CH_2CH_2$— *and the* subscript h is 1, 2, or 3;

D has the formula: $R^4_2 SiO_{2/2}$, where each $R^4$ is independently a monovalent hydrocarbon radical having from one to forty carbon atoms;

D' has the formula: $R^5_{2-i}R^6_i SiO_{2/2}$, where each $R^6$ is independently a monovalent hydrocarbon radical having from one to forty carbon atoms, $R^5$ *is a monovalent hydrocarbon radical selected from the group consisting of* $H_2(OH)CCH(OH)CH_2OCH_2CH_2CH_2$— *and* $(HOCH_2)_2C(CH_2CH_3)CH_2OCH_2CH_2CH_2$— *and the* subscript i is 1 or 2;

T has the formula: $R^7 SiO_{3/2}$, where each $R^7$ is a monovalent hydrocarbon radical having from one to forty carbon atoms;

T' has the formula: $R^8 SiO_{3/2}$, where $R^8$ *is a monovalent hydrocarbon radical selected from the group consisting of* $H_2(OH)CCH(OH)CH_2OCH_2CH_2CH_2$— *and* $(HOCH_2)_2C(CH_2CH_3)CH_2OCH_2CH_2CH_2$— *and* Q has the formula: $SiO_{4/2}$; *and a salt of aluminum or zirconium.*

26. A personal care composition comprising: a silicone compound having *a viscosity greater than about 240 cSts at 25° C. and wherein said silicone compound has* the formula:

$$M_a M'_b D_c D'_d T_e T'_f Q_g,$$

where the subscripts a, b and c are a positive integer, the subscripts d, e, f and g are zero, and the subscript c ranges from 3 to 25;

where M has the formula: $R^1_3SiO_{1/2}$, where each $R^1$ is independently a monovalent hydrocarbon radical having from one to forty carbon atoms;

M' has the formula: $R^2_{3-h}R^3_hSiO_{1/2}$, where each $R^2$ is independently a monovalent hydrocarbon radical having from one to forty carbon atoms, $R^3$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript h is 1, 2, or 3;

D has the formula: $R^4_2SiO_{2/2}$, where each $R^4$ is independently a monovalent hydrocarbon radical having from one to forty carbon atoms;

D' has the formula: $R^5_{2-i}R^6_iSiO_{2/2}$, where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2;

T has the formula: $R^7SiO_{3/2}$, where each $R^7$ is a monovalent hydrocarbon radical having from one to forty carbon atoms;

T' has the formula: $R^8SiO_{3/2}$, where $R^8$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and Q has the formula: $SiO_{4/2}$; and a salt of aluminum or zirconium.

27. A personal care composition comprising: a silicone compound having *a viscosity greater than about 240 cSts at 25° C., and wherein said silicone compound has* the formula:

$$M_aM'_bD_cD'_dT_eT'_fQ_g,$$

where the subscripts a, b and d are a positive integer, the subscripts c, e, f and g are zero, and the subscript [c] *d* ranges from 3 to 25;

where M has the formula: $R^1_3SiO_{1/2}$, where each $R^1$ is independently a monovalent hydrocarbon radical having from one to forty carbon atoms;

M' has the formula: $R^2_{3-h}R^3_hSiO_{1/2}$, where each $R^2$ is independently a monovalent hydrocarbon radical having from one to forty carbon atoms, $R^3$ is a monovalent hydrocarbon radical selected from the group consisiting of $H_2(OH)CCH(OH)CH_2OCH_2CH_2Ch_2$— and $(HOCH_2)_2C(CH_2CH_3)$ $CH_2OCH_2CH_2CH_2$— and the subscript h is 1, 2, or 3;

D has the formula: $R^4_2SiO_{2/2}$, where each $R^4$ is independently a monovalent hydrocarbon radical having from one to forty carbon atoms;

D' has the formula: $R^5_{2-i}R^6_iSiO_{2/2}$, where each $R^6$ is independently a monovalent hydrocarbon radical having from one to forty carbon atoms, $R^5$ is a monovalent hydrocarbon radical selected from the group consisting of $H_2(OH)CCH(OH)CH_2OCH_2CH_2CH_2$— and $(HOCH_2)_2C(CH_2CH_3)CH_2OCH_2CH_2CH_2$— and the subscript i is 1 or 2;

T has the formula: $R^7SiO_{3/2}$, where each $R^7$ is a monovalent hydrocarbon radical having from one to forty carbon atoms;

T' has the formula: $R^8SiO_{3/2}$, where $R^8$ is a monovalent hydrocarbon radical selected from the group consisting of $H_2(OH)CCH(OH)CH_2OCH_2CH_2CH_2$— and $(HOCH_2)_2C(CH_2CH_3)$ $CH_2OCH_2CH_2CH_2$— and Q has the formula: $SiO_{4/2}$, and a salt of aluminum or zirconium.

\* \* \* \* \*